United States Patent [19]

Murata et al.

[11] Patent Number: 5,679,859

[45] Date of Patent: Oct. 21, 1997

[54] PROCESS FOR PRODUCING IMPROVED CRYSTALS OF 3-AMINO-2-HYDROXYACETOPHENONE SALT

[75] Inventors: Hirokazu Murata, Ibaraki; Hideki Ushio; Atsushi Furutani, both of Takatsuki; Hiroaki Hibino, Toyonaka; Etsuko Fukuda, Yamatokoriyama, all of Japan

[73] Assignee: Sumitomo Chemical Company, Ltd., Osaka, Japan

[21] Appl. No.: 616,082

[22] Filed: Mar. 14, 1996

[30] Foreign Application Priority Data

Mar. 14, 1995 [JP] Japan ................... 7-054386

[51] Int. Cl.$^6$ ............................ C07C 209/82
[52] U.S. Cl. .................. 564/438; 564/418; 564/437; 564/439; 564/443
[58] Field of Search .................... 564/418, 437, 564/438, 439, 443

[56] References Cited

FOREIGN PATENT DOCUMENTS 3-95144  4/1991  Japan .

OTHER PUBLICATIONS

WPI Abstract No. 94-147899/ 18 and JP 060092916 A2 (ONO), 1994.

Chemical Abstracts 120:163700 and JP 050279305 A2 (ONO), 1992.

*Primary Examiner*—Richard L. Raymond
*Attorney, Agent, or Firm*—Cushman Darby & Cushman IP Group of Pillsbury Madison & Sutro, LLP

[57] ABSTRACT

The present invention concerns a process for producing crystals of 3-amino-2-hydroxyacetophenone salt having a high bulk density and improved flow properties, by treating 3-amino-2-hydroxyacetophenone of formula (1)

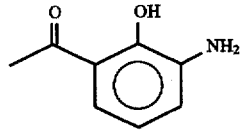

or hydrogen halide salt thereof with sulfuric acid, in a solvent.

22 Claims, No Drawings

PROCESS FOR PRODUCING IMPROVED CRYSTALS OF 3-AMINO-2-HYDROXYACETOPHENONE SALT

FIELD OF THE INVENTION

The present invention relates to a process for producing crystals of 3-amino-2-hydroxyacetophenone salt, which is useful as a pharmaceutical intermediate.

BACKGROUND OF THE INVENTION

A variety of methods have been proposed to manufacture 3-amino-2-hydroxyacetophenone or its acid-added salt. For example, Japanese Patent KOKAI Publication No. 95144/1991 discloses a process defined by the reaction scheme 1 below:

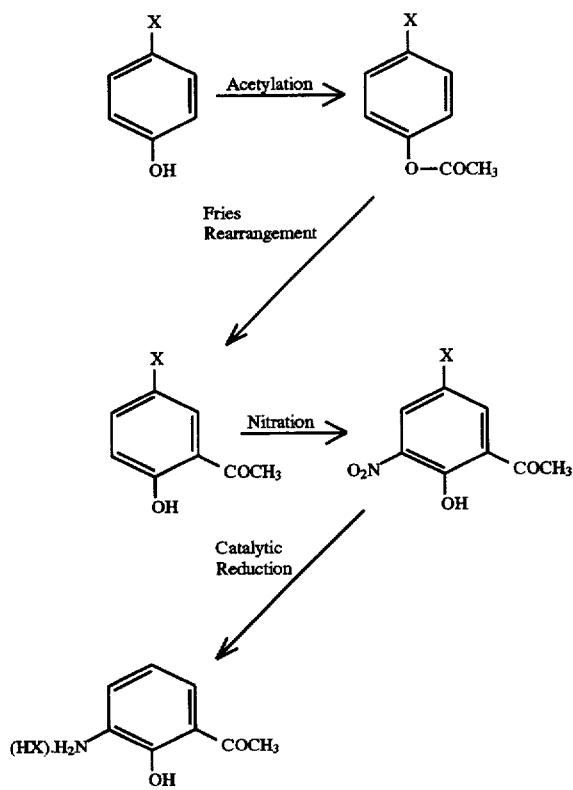

This process for producing 3-amino-2-hydroxyacetophenone has excellent position selectivity in the introduction of acetyl group and nitro group and is thus advantageous over other conventional methods.

As clearly seen in the above reaction scheme, 3-amino-2-hydroxyacetophenone thus obtained reacts with a hydrogen halide produced by the catalytic reduction to form a hydrogen halide salt of 3-amino-2-hydroxyacetophenone. The crystals of hydrogen halide salt result in a low efficiency of isolation procedures including filtration and drying as well as transfer procedures for the isolation. Improvement of the properties of the crystals has been demanded for industrial applications.

Japanese Patent KOKAI Publication No. 95144/1991 also proposes a method of neutralizing the hydrogen halide salt to yield free 3-amino-2-hydroxyacetophenone. The free 3-amino-2-hydroxyacetophenone itself is, however, unstable, and moreover the proposed method requires another time-consuming, quality-degrading and inefficient operation, that is, concentration of the solvent.

SUMMARY OF THE INVENTION

An object of the present invention is to provide a simple and efficient process for producing crystals of 3-amino-2-hydroxyacetophenone salt, which are easily handled for industrial purposes and have high bulk density and improved flow properties. This and other objects and effects of the present invention will become apparent from the following description.

The inventors have studied methods of manufacturing 3-amino-2-hydroxyacetophenone through catalytic reduction of hydroxy-3-nitroacetophenones. As a result of the intensive studies, they have discovered that crystals of 3-amino-2-hydroxyacetophenone salt obtained by treating 3-amino-2-hydroxyacetophenone or its hydrogen halide salt with sulfuric acid have high bulk density and favorable flow properties, whereby problems with the prior art are solved.

Accordingly, the present invention provides a process for producing crystals of 3-amino-2-hydroxyacetophenone salt with high bulk density and improved flow properties, which comprises treating 3-amino-2-hydroxyacetophenone of formula (1)

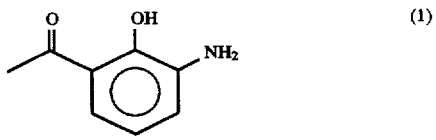

or hydrogen halide salt thereof with sulfuric acid, in a solvent.

DETAILED DESCRIPTION OF THE INVENTION

The 3-amino-2-hydroxyacetophenone represented by formula (1) or its hydrogen halide salt which are to be treated, e.g. starting product or starting materials, can be obtained by catalytic reduction of a nitro compound of formula (2)

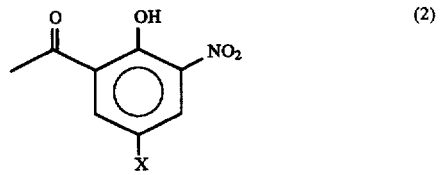

wherein X represents a halogen or hydrogen atom.

The catalytic reduction is usually carried out in a solvent. Typical examples of the solvent used in the reaction include alcohols such as lower alkanols, having 1 to 4 carbon atoms, including methanol, ethanol, and isopropyl alcohol; aromatic hydrocarbons such as benzene, toluene, xylene, and ethylbenzene; halogenated hydrocarbons such as methylene chloride, chloroform, and carbon tetrachloride; ethers such as tetrahydrofuran, dioxane, and diethyl ether; N,N-dimethylformamide, acetic acid, acetic anhydride, water, and mixtures of two or more of these. Alcohols, aromatic hydrocarbons, water, and mixtures of two or more of these are preferred.

The amount of the solvent is usually about 2 to about 10 grams, preferably about 3 to about 6 grams, per gram of nitro compound represented by formula 2.

Examples of catalysts useful in the catalytic reduction include palladium-carbon, palladium black, palladium-alumina, palladium-silica, palladium, platinum dioxide, platinum-carbon, nickel, and Raney nickel. The amount of the catalyst is usually about 0.001 to about 1% by weight, preferably about 0.05 to about 0.25% by weight, in terms of dry metal to nitro compound (2).

The reduction reaction is carried out in an atmosphere of hydrogen at or above ordinary pressure, or more specifically under pressure of about 0 to about 20 kg/cm$^2$G (G means "gauge", and 0 K$_2$/cm$_2$ G is a atmospheric pressure), although the pressure is not restricted to this range.

The reaction temperature is usually about −20° C. to about 100° C., preferably about 10° C. to about 60° C.

This reaction gives 3-amino-2-hydroxyacetophenone or its hydrogen halide salt.

After the reaction is completed, the catalyst is generally removed, e.g. separated from the reaction mixture following the reduction, such as by filtration. When the solvent used in the reaction includes water as a major or primary component, the catalyst is separated by directly filtering the reaction mixture. When X in the nitro compound represented by the formula (2) is a halogen atom and the solvent used in the catalytic reduction reaction is a non-aqueous solvent, such as an alcohol, aromatic hydrocarbon and the like in which hydrogen halide salt of 3-amino-2-hydroxyacetophenone is not substantially dissolved, a base is added to cause 3-amino-2-hydroxyacetophenone to dissolve in the solvent before the catalyst is removed. In the latter case, instead of 3-amino-2-hydroxyacetophenone, an inorganic halide, such as an alkali metal or ammonium halide, e.g., sodium chloride, ammonium chloride, and potassium bromide, is precipitated in the reaction solution. After the treatment with base, the catalyst and the precipitated inorganic halide can be removed simultaneously, such as by filtration.

Useful bases for causing 3-amino-2-hydroxyacetophenone to be soluble in non-aqueous solvents include, for instance, alkali metal carbonates such as sodium carbonate, potassium carbonate and lithium carbonate; alkaline earth metal carbonates such as magnesium carbonate and calcium carbonate; alkali metal bicarbonates such as sodium bicarbonate, potassium bicarbonate and lithium bicarbonate; alkaline earth metal bicarbonates such as magnesium bicarbonate and calcium bicarbonate; alkali metal carboxylates such as sodium acetate, potassium acetate, lithium acetate, sodium propionate, potassium propionate and lithium propionate; alkaline earth metal carboxylates such as magnesium acetate, calcium acetate, magnesium propionate and calcium propionate; alkali metal hydroxides such as sodium hydroxide, potassium hydroxide and lithium hydroxide; alkaline earth metal hydroxides such as magnesium hydroxide and calcium hydroxide; alkyl amines such as triethylamine and diethylamine; pyridines such as pyridine and picoline; and ammonia. For the easy removal of the deposited inorganic halide, sodium acetate, sodium bicarbonate, sodium carbonate, and ammonia are preferred. The amount of base should be sufficient to make 3-amino-2-hydroxyacetophenone dissolve in the solvent, and is usually 0.1 to 3 equivalents, preferably 0.5 to 1.2 equivalents.

The addition of the base is carried out at a temperature which is usually in a range from about −20° C. to about 100° C. or to the boiling point of the solvent to be used, and is preferably from about 10° C. to about 60° C.

The removal of catalyst is carried out usually at a temperature in a range from about −20° C. to about 100° C. or to its boiling point, preferably at from about 10° C. to about 60° C.

The solution of 3-amino-2-hydroxyacetophenone or its hydrogen halide salt after the catalytic reduction and/or removal of the catalyst can be subjected to the sulfuric acid treatment. Although the 3-amino-2-hydroxyacetophenone (1) or its hydrogen halide salt thus obtained can be isolated by distillation, recrystallization, or another treatment, the reaction solution after the removal of the catalyst is generally used as the raw material which is treated with sulfuric acid, in a solvent according to the present invention.

The nitro compound of formula (2) is known and can be prepared, for example, according to the method disclosed in Japanese Patent KOKAI Publication No. 95144/91, the complete disclosure of which is incorporated herein by reference.

The crystals of 3-amino-2-hydroxyacetophenone salt having a high bulk density and an improved flow are obtained by treating 3-amino-2-hydroxyacetophenone or its hydrogen halide salt with sulfuric acid in a solvent.

The sulfuric acid used is 30% to 98% sulfuric acid or fuming sulfuric acid, and is preferably 70% to 98% sulfuric acid.

A general method of treating 3-amino-2-hydroxyacetophenone or its hydrogen halide salt with sulfuric acid comprises adding sulfuric acid to 3-amino-2-hydroxyacetophenone or its hydrogen halide salt in a solution, or a suspension or slurry in a solvent to contact 3-amino-2-hydroxyacetophenone or its hydrogen halide salt with the sulfuric acid.

Typical examples of the solvent used include alcohols such as methanol, ethanol, and isopropyl alcohol; aromatic hydrocarbons such as benzene, toluene, xylene, and ethylbenzene; halogenated hydrocarbons such as methylene chloride, chloroform, and carbon tetrachloride; ethers such as tetrahydrofuran, dioxane, and diethyl ether; N,N-dimethylformamide; acetic acid; acetic anhydride; water; and mixtures of two or more of these.

The amount of solvent depends upon the type of solvent used in the sulfuric acid treatment step, but is suitably selected within a range generally from about 2 to about 10 times the weight of 3-amino-2-hydroxyacetophenone or its hydrogen halide salt to be treated.

The amount of sulfuric acid is generally from about 1 to about 10 moles, preferably about 2 to 4 moles, per one mole of 3-amino-2-hydroxyacetophenone or its hydrogen halide salt.

The treatment temperature is generally about −20° C. to about 100° C. or to the boiling point of the solvent to be used, and more preferably is in the range of from about 10° C. to about 60° C.

The sulfuric acid is usually added in 0.1 to 10 hours, and is preferably added in 1 to 5 hours.

Vessels useful for conducting the sulfuric acid treatment are not particularly limited as long as the solution, suspension or slurry of the 3-amino-2-hydroxyacetophenone or its hydrogen halide salt can be stirred and sulfuric acid can be added.

After the addition of sulfuric acid, if necessary, the sulfuric acid treated mixture may be aged for 1 to 3 hours.

Generally, the 3-amino-2-hydroxyacetophenone salt crystallizes out.

However, in case the treatment with sulfuric acid in water or solvent containing water as a major component results in insufficient precipitation of the crystals of 3-amino-2-hydroxyacetophenone salt, e.g. when the amount of precipitated crystals is small, a solvent in which 3-amino-2-hydroxyacetophenone salt has poor solubility, for example, an alcohol or ether such as tetrahydrofuran, may be added before, in the course of, or after the treatment with sulfuric acid to accelerate the crystallization. Another possible method is to remove water with another solvent by azeotrope. This method is, however, less favored because it's energy inefficient and time-consuming.

It is preferred that the solvent substantially consists of an alcohol or a hydrocarbon or includes an alcohol or a hydrocarbon as a major component (generally containing an alcohol or hydrocarbon of not less than about 70% by weight).

The crystals of 3-amino-2-hydroxyacetophenone salt obtained by the treatment with sulfuric acid are separated from the solvent for example by filtration. Separation at a lower temperature is more preferable in order to obtain a higher yield of the crystals. In industrial applications, the separation is carried out at a temperature usually from about −20° C. to about 20° C.

Filtration of the crystals of 3-amino-2-hydroxyacetophenone salt can be carried out by filtration under reduced pressure, filtration under pressure, and filtration at ordinary pressure. Filtration under pressure and centrifugal filtration are industrially preferred.

The crystals separated from the solvent by filtration can be dried by methods known to those skilled in the art, such as, for example, by vacuum drying and flow through drying.

The crystals of 3-amino-2-hydroxyacetophenone salt thus obtained have a high bulk density. In the specification and claims, the bulk density value of crystals of a compound is indicated by reciprocal number of ordinal value of density as (volume of crystals of a compound)/(weight of the crystals at the volume)(ml/g). Therefore, a lower value means a higher bulk density and a higher value means a lower bulk density. The bulk density is generally from about 0.5 to about 10 ml/g, preferably from 0.5 to 6 about ml/g, more preferably about 0.5 to about 4 ml/g, when measuring weight of a compound of predetermined volume. The crystals also improve the poor flow property of the hydrochloride or another salt and have an angle of repose which is analyzed by pouring method (e.g. using PT-N type detector of angel of repose manufactured by Hosokawa Micron Kabushikigaisha and FK type detector manufactured by Tsutsui Rikagaku Kikai Kabushikigainsha), of usually not larger than 60 degrees, preferably not larger than 55 degrees, more preferably not larger than 50 degrees by a known detecting apparatus for angle of repose.

As discussed above, the methods of the present invention can provide crystals of 3-amino-2-hydroxyacetophenone salt which have a high bulk density and exhibit an improved flow and are useful as an intermediate in the preparation of pharmaceuticals. The present invention is industrially advantageous because the 3-amino-2-hydroxyacetophenone salt is obtained at a remarkably high productivity and by a simple process.

A method for producing the crystals as disclosed herein is described in Japanese Application 07-054386 filed Mar. 14, 1995, the complete disclosure of which is incorporated herein by reference.

EXAMPLES

The present invention is further described by the following examples, but it is not restricted to these examples.

The nitro compounds of formula (2) used in the following examples were synthesized according to the method disclosed in Japanese Patent KOKAI Publication No. 95144/1991.

Examples 1–8

Preparation of 3-amino-2-hydroxyacetophenone salt (1) 40 g of 5-chloro-2-hydroxy-3-nitroacetophenone and 1.75 g of 5% palladium-carbon (water content: 55%) were added to 200 g of each reaction solvent specified in Table 1, and the mixture was subjected to catalytic reduction in an atmosphere of hydrogen at ordinary pressure and temperature between 25° C. and 50° C. When the completion of the catalytic reduction was confirmed by high performance liquid chromatography (column: SUMIPAX ODS A-212 manufactured by Sumika Chemical Analysis Service Ltd., carrier, (20 mmol $K_3PO_4$ in water)/$CH_2C_N$; 55/45), the reaction mixture was a slurry of 3-amino-2-hydroxyacetophenone hydrochloride salt. In each of Examples 1–8, a base as specified in Table 1 was added to the reaction mixture in an amount of 0.9 equivalent to nitro compound (2). After stirring at 50° C. for 30 minutes, the deposited catalyst and inorganic halide were removed by filtration.

(2) After 56.1 g of 98% aqueous sulfuric acid was added dropwise to the filtrate at the temperature of 50° C. over 1 hour, the mixture was kept at the same temperature for 1 hour and then gradually cooled to 0° C. The crystals thus deposited were filtered out at the temperature of 0° C. The crystals separated out were dried under reduced pressure, and the bulk density of the crystals was measured using a measuring flask and the angle of repose as an indication of the flow properties, was measured using detector for the angle of repose manufactured by Tsutsui Rikagaku Kikai Kabushikigaisha. Results of the measurement are shown in Table 1 below.

| Examples | Solvents | Bases | Yield of crystals (%) | Bulk density of crystals (ml/g) | Angle of repose of crystals (°) |
|---|---|---|---|---|---|
| 1 | Ethanol | NaOAc | 80 | 2.0 | 38 |
| 2 | Ethanol | NaHCO$_3$ | 78 | 2.4 | 42 |
| 3 | Ethanol | 20% aq.NaHCO$_3$ | 70 | 2.6 | 46 |
| 4 | Ethanol | 28% aq.NH$_3$ | 73 | 2.6 | 46 |
| 5 | Methanol | NAOAC | 58 | 2.5 | 45 |
| 6 | Methanol | NaHCO$_3$ | 54 | 2.7 | 44 |
| 7 | i-propanol | NaOAC | 79 | 2.6 | 41 |
| 8 | i-propanol | NaHCO$_3$ | 76 | 2.7 | 43 |

Example 9

(1) 34 g of 2-hydroxy-3-nitroacetophenone and 1.75 g of 5% palladium-carbon (water content: 55%) were added to 200 g of ethanol, and the mixture was subjected to catalytic reduction in an atmosphere of hydrogen at ordinary pressure and a temperature of 25° C. After the completion of the catalytic reduction, the catalyst was removed by filtration at 40° C.

(2) After 56.1 g of 98% aqueous sulfuric acid was added dropwise to the filtrate at the temperature of 40° C. over 1 hour, the mixture was kept at the same temperature for 1 hour and then gradually cooled to 0° C. whereby, crystals were deposited. The deposited crystals were filtered out at a temperature of 0° C. The crystals separated out were dried under reduced pressure. The yield was 38.4 g, the bulk density of the crystals obtained was 2.1 (ml/g), and the angle of repose was 40 degrees.

Comparative Examples 1–3

Preparation of 3-amino-2-hydroxyacetophenone hydrochloride

The procedure of Example 1 (1) was repeated except that each base specified in Table 2 was added to the reaction solution. After 28.9 g of 35% aqueous hydrochloric acid was added dropwise to the filtrate thus obtained at the same temperature of 50° C. over 1 hour, the mixture was kept at the same temperature for 1 hour and then gradually cooled to 0° C. whereby crystals were deposited. The deposited crystals were filtered out at a temperature of 0° C. and dried under reduced pressure. The bulk density of the crystals and the angle of repose as an indication of flow properties were measured. Results of the measurement are shown in Table 2.

TABLE 2

| Comparative Examples | Solvents | Bases | Yield of crystals (%) | Bulk density of crystals (ml/g) | Angle of repose of crystals (°) |
|---|---|---|---|---|---|
| 1 | Ethanol | NaOAc | 76 | 9.8 | 68 |
| 2 | Ethanol | NaHCO$_3$ | 78 | 10.8 | 69 |
| 3 | Ethanol | Mg(OH)$_2$ | 77 | 9.2 | 65 |

Example 10

A slurry consisting 20 g of 3-amino-2-hydroxyacetophenone hydrochloride and 100 g of ethanol was charged into a reaction vessel and heated to the temperature of 50° C. After 98% aqueous sulfuric acid was added dropwise to the slurry at the temperature of 50° C., the mixture was kept at the temperature of 50° C. for 1 hour and then gradually cooled to 2° C. whereby crystals were deposited. The deposited crystals were filtered out at a temperature of 2° C. and dried under reduced pressure. The bulk density of the crystals and the angle of repose as an indication of flow properties were measured. The results showed the bulk density of crystals was 3.1 (ml/g), angle of repose was 51 degree and yield was 85%.

What is claimed is:

1. A process for producing crystals of 3-amino-2-hydroxyacetophenone salt which have high bulk density of from about 0.5 to about 10 ml/g and an angle of repose of not larger than 60 degrees, which comprises the step of treating 3-amino-2-hydroxyacetophenone of the formula (1)

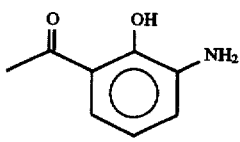

or hydrogen halide salt thereof with sulfuric acid, in a solvent.

2. A process according to claim 1, wherein said 3-amino-2-hydroxyacetophenone or hydrogen halide salt thereof is 3-amino-2-hydroxyacetophenone or the hydrochloride salt thereof.

3. A process according to claim 1, wherein 1 to 10 moles of sulfuric acid is used per one mole of said 3-amino-2-hydroxyacetophenone or hydrogen halide salt thereof.

4. A process according to claim 1, wherein an amount of sulfuric acid is 2 to 4 moles per one mole of said 3-amino-2-hydroxyacetophenone or hydrogen halide salt thereof.

5. A process according to claim 1, wherein said solvent consists essentially of an alcohol or an aromatic hydrocarbon.

6. A process according to claim 1, wherein said solvent contains at least 70% by weight of an alcohol or an aromatic hydrocarbon.

7. A process according to claim 1, wherein said solvent consists essentially of an alcohol.

8. A process according to claim 1, wherein said solvent contains at least 70% by weight of an alcohol.

9. A process according to claim 1, wherein said crystals of 3-amino-2-hydroxyacetophenone salt produced have a bulk density of from 0.5 to 6 ml/g.

10. A process according to claim 1, wherein said crystals of 3-amino-2-hydroxyacetophenone salt produced have a bulk density of from 0.5 to 4 ml/g.

11. A process according to claim 1, wherein said 3-amino-2-hydroxyacetophenone and/or hydrogen halide salt thereof to be treated with sulfuric acid is obtained by reducing a nitro compound represented by formula (2)

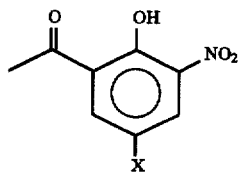

wherein X represents a halogen atom or hydrogen atom in the presence of a catalyst.

12. A process according to claim 1, wherein said 3-amino-2-hydroxyacetophenone and/or hydrogen halide salt thereof used as starting product is obtained by reducing a nitro compound represented by formula (2)

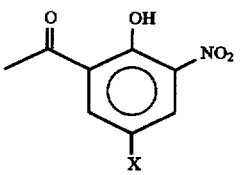

wherein X represents a halogen atom or hydrogen atom, in the presence of a catalyst, and subsequently removing said catalyst.

13. A process according to claim 12, wherein a base is added to the reaction mixture after reducing said nitro compound but before removing said catalyst.

14. A process according to claim 13, wherein the base is selected from the group consisting of alkali metal carbonates, alkaline earth metal carbonates, alkali metal bicarbonates, alkaline earth metal bicarbonates, alkali metal carboxylates, alkaline earth metal carboxylates, alkali metal hydroxides, alkaline earth metal hydroxides, alkyl amines, pyridines and ammonia.

15. A process according to claim 1, wherein the angle of repose is not larger than 55 degrees.

16. A process according to claim 15, wherein the angle of repose is not larger than 50 degrees.

17. A method of raising the bulk density of 3-amino-2-hydroxyacetophenone salt crystals to about 0.5 ml/g to about 10 ml/g, which comprises the step of contacting 3-amino-2-hydroxyacetophenone of the formula (1)

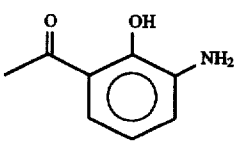

or hydrogen halide salt thereof with 30 to 98% sulfuric acid or fuming sulfuric acid, in a solvent, wherein the resulting 3-amino-2-hydroxyacetophenone salt crystals have an angle of repose of not larger than 60 degrees.

18. A method of improving the flow property of 3-amino-2-hydroxyacetophenone salt crystals, which comprises the step of contacting 3-amino-2-hydroxyacetophenone of the formula (1)

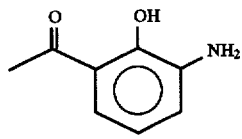

or hydrogen halide salt thereof with sulfuric acid, in a solvent at a temperature of from about −20° C. to 100° C. or to the boiling point of the solvent, wherein the resulting 3-amino-2-hydroxyacetophenone salt crystals have an angle of repose of not larger than 60 degrees and a bulk density of about 0.5 to about 10 ml/g.

19. A method according to claim 17, wherein said angle of repose is not larger than 55 degrees.

20. A method according to claim 19, wherein said angle of repose is not larger than 50 degrees.

21. A method according to claim 18, wherein said angle of repose is not larger than 55 degrees.

22. A method according to claim 21, wherein said angle of repose is not larger than 50 degrees.

* * * * *